United States Patent [19]

Rutzen

[11] Patent Number: 4,480,126

[45] Date of Patent: Oct. 30, 1984

[54] PROCESS FOR THE PREPARATION OF QUATERNARY AMMONIUM COMPOUNDS

[75] Inventor: Horst Rutzen, Langenfeld, Fed. Rep. of Germany

[73] Assignee: Henkel Kommanditgesellschaft auf Aktien, Duesseldorf, Fed. Rep. of Germany

[21] Appl. No.: 369,759

[22] Filed: Apr. 19, 1982

[30] Foreign Application Priority Data

Sep. 15, 1981 [DE] Fed. Rep. of Germany ....... 3136628

[51] Int. Cl.[3] .............................................. C07C 91/40

[52] U.S. Cl. .................................... 564/292; 564/285; 564/296; 564/295; 564/293; 564/286; 424/329; 252/8.8; 252/81.1

[58] Field of Search ............... 564/285, 276, 292, 293, 564/290, 295, 286

[56] References Cited

U.S. PATENT DOCUMENTS

| | | | |
|---|---|---|---|
| 2,142,140 | 1/1939 | Major et al. | 564/293 |
| 2,192,925 | 3/1940 | Major et al. | 564/293 |
| 2,655,541 | 10/1953 | Hopff | 564/293 |
| 3,373,201 | 3/1968 | Eygen | 564/293 |

FOREIGN PATENT DOCUMENTS 1652365 3/1963 Japan .

OTHER PUBLICATIONS

Komkov et al., Chem. Abst., vol. 79, #147612r (1973).

J. Goerdeler in Houben-Weyl, Methoden der Organischer Chemie. 4th Edition, vol. 11/12, pp. 592 et seq.

*Primary Examiner*—James H. Reamer

*Attorney, Agent, or Firm*—Ernest G. Szoke; Henry E. Millson, Jr.; Mark A. Greenfield

[57] ABSTRACT

Process for the preparation of quaternary ammonium compounds by reacting a tertiary amine with a vicinal halohydrin having at least 6 carbon atoms, and quaternary ammonium compounds prepared thereby.

9 Claims, No Drawings

PROCESS FOR THE PREPARATION OF QUATERNARY AMMONIUM COMPOUNDS

BACKGROUND OF THE INVENTION

The manufacture of quaternary ammonium compounds is generally carried out by alkylating a tertiary amine to the quaternary stage. The alkylating agent is usually an ester of a strong mineral acid, especially sulfuric or sulfonic acid esters, or an alkyl halide, for reaction with the tertiary amine. Occasionally, other esters are employed. Another known method for alkylating tertiary amines is by reacting alkylene oxides with tertiary amines in the presence of water. A number of other procedures can also be employed to manufacture quaternary ammonium compounds from readily available tertiary amines. See, e.g., J. Goerdeler in Houben-Weyl, Methoden der organischer Chemie, 4th Edition, Vol. 11/12, pages 592 et seg.

Quaternary ammonium compounds with one or more long aliphatic radicals, or one long aliphatic radical and one aromatic radical exhibit antimicrobial as well as textile softening and antistatic properties, and they are used extensively for these purposes. Such compounds are obtained either by alkylating tertiary amines having long aliphatic groups and/or aromatic groups, or by alkylating with alkylating agents that contain long aliphatic or aromatic groups. Obviously, the tertiary amine as well as the alkylating agent can each contain long aliphatic and/or aromatic groups.

The disadvantage of the known processes for the manufacture of quaternary ammonium compounds is that usually pressure must be used, and occasionally solvents are also required. In addition, the yield is usually disappointing. In German patent application No. P31 16 087.5 (D6299), which was not pre-published, it was suggested that epoxide compounds having terminal epoxide groups be employed, together with the salt of a tertiary amine in the presence of a quaternary ammonium compound as the catalyst for the reaction.

It is also known that quaternarization of tertiary amines can be carried out using halohydrins, see e.g. Japanese patent application No. 16 523/65, where the reaction of trimethylamine with ethylene chlorohydrin to choline chloride is described. The use of halohydrins for quaternarizing has also been known from the literature, but only with respect to the use of ethylene chlorohydrin.

DETAILED DESCRIPTION OF THE INVENTION

It has now surprisingly been found that quaternary ammonium compounds can be manufactured in an aqueous system by reacting a tertiary amine with a vicinal halohydrin having at least 6 carbon atoms, using heat at normal atmospheric pressure. It could not have been anticipated that higher molecular weight halohydrins would react readily with tertiary amines based on a knowledge of the reactions of ethylene chlorohydrin, particularly since the reaction mixture consisting of higher molecular weight halohydrins and tertiary amines is a two-phased mixture in the presence of water.

Halohydrins that are employed in the process of the invention are 1,2-halohydrins having a straight or branched chain alkyl group of at least 6 carbon atoms and preferably from 6 to 28 carbon atoms, i.e. such halohydrins have either the hydroxyl group or the halogen atom attached to a terminal carbon atom, with the other group or atom attached to the carbon atom immediately adjacent thereto. The halogen atom can be chlorine, bromine, or iodine. Also, $C_6$–$C_{28}$ halohydrins having an ether linkage between the 3rd and 5th carbon atoms counting from one or both terminal carbon atoms of the chain (i.e. derived from mono or diglycidyl ether precursors, as discussed later) can also be used in the process of the invention. In addition, $C_6$–$C_{28}$ bis halohydrins having the halohydrin structure at each end of the carbon chain can be employed herein. Especially useful 1,2-halohydrins for use in the present process are 1,2-halohydrins (with or without an ether linkage) with 10 to 20, preferably 12 to 16 carbon atoms, such as 1(2)-chloro-2(1)-hydroxy-dodecane, 1(2)-bromo-2(1)-hydroxy-hexadecane, 1(2)-chloro-2(1)-hydroxy-hexadecane, and 1(2)-iodo-2(1)-hydroxy-dodecane, where the designation 1(2)- or 2(1) includes the pure isomers as well as their mixture.

The reaction of the halohydrin with a tertiary amine is preferably carried out at a 1:1 mole ratio. However, a slight excess of one or the other of the components can be used and may in some instances be advantageous.

Tertiary amines which are suitable as reactants with the halohydrins used in the process of the invention are the more strongly basic tertiary amines, e.g. those having one or more straight or branched chain alkyl, hydroxyalkyl, or aralkyl (e.g. benzyl, phenylethyl, etc.) groups, or an N-heterocyclic group containing the nitrogen atom of the tertiary amine in the ring structure, wherein such groups contain less than 10 carbon atoms, and wherein the tertiary amine can optionally contain a $C_{10}$ to $C_{20}$ straight or branched chain alkyl or alkenyl group. Examples of such tertiary amines include the trialkylamines, e.g. trimethylamine, triethylamine, tributylamine, dimethylhexylamine, dimethyllaurylamine; the dialkyl aralkylamines, e.g. dimethylbenzylamine; tertiary amines containing one or more hydroxyalkyl groups, dimethylethanolamine, dimethylpropanolamine, N-$\beta$-hydroxydecyl-N-$\beta$-hydroxyethyl-N-methylamine, N-$\beta$-hydroxyhexadecyl-N-$\beta$-hydroxyethyl-N-methylamine, methyldiethanolamine, dimethylaminopropanediol; tertiary diamines such as tetramethylethylenediamine, or tetramethyl propylenediamine-1,3; and, additionally, heterocyclic tertiary amines having the nitrogen atom in the ring structure, e.g. pyridine, picoline, pipecoline, N-methylpiperidine, N-methylpyrrolidine, quinuclidine, etc.

The present process should be carried out at an elevated temperature, i.e. from about 40° to about 100° C., preferably from about 65° to about 95° C. An addition of from about 0.5 to about 10 wt %, based on the weight of the end product, of a quaternary ammonium salt will speed up the reaction.

The 1,2-halohydrins having at least 6 carbon atoms which are used as a reactant in the present process are easily obtained, for example, by the reaction between a 1,2-epoxyalkane having at least 6 carbon atoms and a hydrogen halide. The reaction is preferably carried out with the above reactants in a 1:1 mole ratio. The corresponding halohydrin is obtained in practically quantitative yield from the 1,2-epoxyalkane within a relatively short reaction time. The hydrogen halide can be used in a commercially available concentrated aqueous form, such as 37% HCl; 48% or 63% HBr; or 57% or 67% HI. The reaction temperature is preferably from about 30° to about 100° C. Such temperatures are normally obtained without external heating due to the heat of reaction. The reaction mixture is two-phased when using aqueous hydrogen halide solutions and the reaction will be completed within about one hour. If aqueous hydrogen halide solutions in dilute concentrations are used, the reaction will take a longer time. Instead of using aqueous solutions, the halohydrins can also be obtained when using gaseous or dry hydrogen halide. The halohydrin reaction product obtained from the above described process is usually not uniform; i.e. the reaction mixture consists of a mixture of isomers of 1-halogen-2-hydroxyalkane and 1-hydroxy-2-halogenalkane. A separation of these isomers is not necessary for use in the process of the invention.

Suitable 1,2-epoxyalkanes for the manufacture of the 1,2-halohydrins used in the process of the invention are obtained from the appropriate 1,2-monolefin or olefin mixtures by known methods, such as by the polymerization of ethylene using organic aluminum compounds as catalysts, or by thermal cracking of paraffin hydrocarbons. Examples of preferred 1,2-epoxyalkanes are 1,2-epoxyhexane, 1,2-epoxydecane, 1,2-epoxydodecane, 1,2-epoxytetradecane, 1,2-epoxyhexadecane, and 1,2-epoxyoctadecane. Also Suitable are epoxide mixtures such as $C_{12/14}$-1,2-epoxide with about 70 weight percent $C_{12}$- and about 30 weight percent $C_{14}$-epoxyalkane or $C_{16/18}$-1,2-epoxide with about 40 weight percent $C_{16}$- and about 60 weight percent $C_{18}$-epoxyalkane. In addition, a diepoxyalkane having at least 6, and preferably 8 to 20 carbon atoms and two terminal epoxy groups can also be used, such as 1,2-7,8-diepoxyoctane, 1,2-9,10-diepoxydecane, and similar compounds. Also, mono- or di-glycide ethers such as hexadecyl monoglycide ether and 1,4-butanediol-diglycide ether are useful epoxide compounds having terminal epoxide groups. The preferred epoxide compounds that can be employed are either (a) those of the general formula:

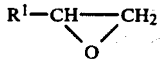
(I)

wherein $R^1$ is either a straight or branched chain aliphatic hydrocarbon group having 4 to 21 carbon atoms, or a group of the general formula:

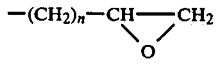
(II)

wherein n is an integer of from 4 to 16; or (b) glycide ethers of the general formula:

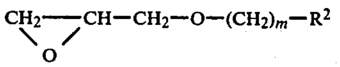
(III)

wherein m is an integer of from 1 to 10, and $R^2$ is hydrogen, or an aliphatic straight or branched chain hydrocarbon group having from 1 to 24 carbon atoms, or a group of the general formula:

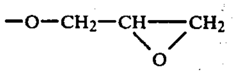
(IV)

and provided that the glycide ethers of formula III contain a total of at least 6 carbon atoms.

The present process has marked advantages over prior art processes for preparing the quaternary ammonium products of the process. For example, the present process does not require pressures above atmospheric. Also, only relatively low reaction temperatures and short reaction times are required. Furthermore, the products of the reaction are of high purity and are obtained in high yield.

The reaction products of the present process are useful as textile softeners, anti-static agents, and/or as antibacterial agents for application to surfaces to be disinfected such as containers used in the food industry.

Particularly useful antibacterial products can be obtained from the process of the invention by either (a) reacting a halohydrin (with or without an ether linkage) having from 10 to 20 carbon atoms with a tertiary amine having one or more alkyl, hydroxyalkyl or aralkyl groups wherein each group contains fewer than 10 carbon atoms, or (b) reacting a halohydrin (with or without an ether linkage) having from 6 to 10 carbon atoms with a tertiary amine containing a $C_{10}$ to $C_{20}$ alkyl or alkenyl group.

Quaternary ammonium compounds having excellent antistatic and/or textile softening properties can be obtained from the process of the invention by reacting a halohydrin (with or without an ether group) having at least 6 carbon atoms with a tertiary amine having a $C_{10}$ to $C_{20}$ alkyl or alkenyl group. It has been found that as the number and chain length of the long chain alkyl or alkenyl group increases, the reaction products exhibit gradually increasing textile softening and antistatic properties. Accordingly, the most preferred compounds for these utilities are those formed by the reaction between a tertiary amine that contains a $C_{10}$ to $C_{20}$ alkyl or alkenyl group with a halohydrin (with or without an ether linkage) having 10 to 20 carbon atoms to produce a quaternary ammonium compound having a $C_{10}$–$C_{20}$ alkyl or alkenyl group, and a $C_{10}$–$C_{20}$ hydroxyalkyl or hydroxyalkylether group.

The use of the above products as textile softeners can be in liquid products such as liquids for after treating clean laundry. Such liquids may contain, in addition to one or more of the above products, carrier substances, solvents, diluents, emulsifiers, coloring agents, and/or other commonly used additives.

An example of a compositon useful as a laundry aftertreatment is as follows:

2–80 wt % of a quaternary ammonium compound having a $C_{10}$–$C_{20}$ alkyl or alkenyl group, and a $C_{10}$–$C_{20}$ hydroxyalkyl or hydroxyalkylether group
20–98 wt % of carriers, solvents and/or diluents
0–20 wt % emulsifier
0–3 wt % preservative
0–5 wt % perfume
0–1 wt % coloring agent Also, the quaternary ammonium compounds produced by the process of the invention can be added to detergent formulations which contain at least one laundry-active compound to produce a softening effect on the laundry. Such detergent formulations are usually based on formulations containing nonionic surfactants. Furthermore, the products of the invention can be applied to textile surfaces as an aid in tumbling.

The invention will be better understood from the following examples which are given for illustration purposes only and not to limit the invention.

EXAMPLE 1

123.8 g (0.5 mole) of 1,2-epoxy hexadecane (epoxide number 6.46) was mixed with stirring with 49.3 g (0.5 mole) of aqueous, concentrated HCl (37%). During the mixing the temperature rose to 65° C. The reaction mixture was then maintained at 95° C. for 1 hour. 44.6 g (0.5 mole) of dimethylethanolamine and 732 g water was then added to the reaction mixture, and the temperature maintained for 8 hours at 95° C. The amine number decreased to 2. The clear, homogeneous solution contained 95% of the theoretically possible quantity of quaternary ammonium salt.

EXAMPLE 2

94.3 g (0.5 mole) 1,2-epoxydodecane (epoxide number 8.48) was mixed with 49.3 g (0.5 mole) of 37% aqueous HCl, and maintained at 95° C. for 1 hour. 67.6 g (0.5 mole) of dimethylbenzylamine, and 500.8 g water was added and heated with stirring at 95° C. for 8 hours. The initial two-phase reaction mixture became homogeneous and the amine number decreased to 2.3, The solution contained 92% of the theoretically possible quantity of quaternary ammonium salt.

EXAMPLE 3

81.6 g (0.5 mole) of 49.6% HBr were added with stirring to 123.8 g (0.5 mole) of 1,2-epoxyhexadecane, (epoxide number 6,46) during which the temperature rose to 65° C. After one hour at 95° C., no epoxide was present and after cooling, the bromhydrin crystallized. 44.6 g (0.5 mole) of dimethylethanolamine and 585.4 g water was added and stirred for 8 hours at 95° C. The amine number decreased to 2.1. The reaction product, which solidified into a clear gel during cooling, contained 96.2% of the theoretically possible quantity of quaternary ammonium salt.

EXAMPLE 4

A mixture consisting of 94.3 g (0.5 mole) of 1,2-epoxydodecane (epoxide number 8.48) and 111.2 g (0.5 mole) of 57.5% HI was stirred at 95° C. for 4 hours. 44.6 g (0.5 mole) of dimethylethanolamine was added and the reaction mixture was stirred for 6 hours at 95° C. The amine number of the homogenous clear solution was 0.9, and the quantity of quaternary ammonium salt present was about 92% of the theoretically possible amount.

EXAMPLE 5

94.3 g (0.5 mole) of 1,2-epoxydodecane (epoxide number 8.48), 111.2 g (0.5 mole) of 57.5% HI and 486.9 g of water were stirred at 95° C. for 75 minutes. 72.3 g (0.57 mole) of 47% aqueous trimethylamine solution was added and stirred for 4 hours at 95° C. The amine number was 0.72, and the conversion of quaternary ammonium salt was complete for all practical purposes.

EXAMPLE 6

A mixture of 94.3 g (0.5 mole) of 1,2-epoxydodecane and 51.64 g (0.5 mole) of 35.3% HCl was stirred for 1 hour to convert the epoxide to the corresponding chlorhydrin. 410.8 g water and 35.5 g (0.27 mole) of tetramethylpropylenediamine-1,3 was added and heated to 95° C. for 8 hours. A homogenous clear solution was obtained. The conversion to the quaternary ammonium salts was substantially quantitative.

EXAMPLE 7

80.6 g (0.5 mole) of 1,2-epoxydecane (epoxide number 9.93) and 49.27 g (0.5 mole) of 37% HCl were heated to 95° C. with stirring for 1 hour. The epoxide number registered zero. After adding 646.2 g water and 129.5 g (0.5 mole) of methyl-2-hydroxydodecylethanolamine (amine number 216.7) the resulting mixture was heated to 95° C., and stirred for 25 hours. A clear, yellowish gel was obtained with an amine number of 6.1. The conversion to quaternary ammonium salt was almost quantitative.

Results comparable to those obtained in the above examples using similar conditions, but employing other tertiary amines having a fatty alkyl group such as dimethyl-cocoa alkylamine, dimethyltallowakylamine, di ethyltallowalkylamine, etc., were also obtained using the process of the invention.

What is claimed is:

1. A process for the preparation of a quaternary ammonium compound comprising reacting together a tertiary amine and a vicinal halohydrin at a temperature in the range of from about 40° C. to about 100° C. in an aqueous system under normal atmospheric pressure, wherein the constituents on the tertiary amine consist essentially of one or more alkyl, hydroxyalkyl, or aralkyl groups, or an N-heterocyclic group having the nitrogen atom of the tertiary amine in the ring structure, wherein such groups each contain less than 10 carbon atoms, and wherein the halohydrin is a 1,2 halohydrin containing from 6 to 28 carbon atoms.

2. A process in accordance with claim 1 wherein the tertiary amine and the halohydrin are present in approximately equivalent quantities.

3. A process in accordance with claim 1 wherein the halohydrin contains from 10 to 20 carbon atoms.

4. A process in accordance with claims 1 or 6 wherein the tertiary amine contains an alkyl or alkenyl group having from 10 to 20 carbon atoms.

5. A process in accordance with claim 1 wherein from about 0.5 to about 10% by weight, based on the theoretical weight of the quaternary ammonium compound reaction product, of a quaternary ammonium salt is added to the reaction mixture.

6. A process in accordance with claim 1 wherein the halohydrin is a bis halohydrin.

7. A process in accordance with claim 1 wherein the halohydrin has an ether linkage between the 3rd and 5th carbon atoms counting from one or both terminal carbon atoms of the carbon chain thereof.

8. A process in accordance with claim 1 wherein the temperature is in the range of from about 65° to about 95° C.

9. A process in accordance with claim 1 wherein the halohydrin contains from 12 to 16 carbon atoms.

* * * * *